(12) United States Patent
Petzelt

(10) Patent No.: US 6,171,818 B1
(45) Date of Patent: Jan. 9, 2001

(54) PROTEIN HAVING AN ANTI-TUMORAL EFFECT

(75) Inventor: Christian Petzelt, Berlin (DE)

(73) Assignee: Bioxen Ltd, St. Helier/Jersey (GB)

(*) Notice: Under 35 U.S.C. 154(b), the term of this patent shall be extended for 0 days.

(21) Appl. No.: 09/068,097
(22) PCT Filed: Oct. 31, 1996
(86) PCT No.: PCT/DE96/02104
§ 371 Date: Sep. 22, 1998
§ 102(e) Date: Sep. 22, 1998
(87) PCT Pub. No.: WO97/16457
PCT Pub. Date: May 9, 1997

(30) Foreign Application Priority Data

Nov. 2, 1995 (DE) .............................. 195 40 902

(51) Int. Cl.[7] .............................. C12P 21/06; C07K 14/00
(52) U.S. Cl. ..................... 435/69.1; 435/320.1; 435/325; 435/252.3; 530/300; 514/12
(58) Field of Search .................................... 435/69.1, 325, 435/320.1; 530/300; 514/12

(56) References Cited

PUBLICATIONS

Takamatsu, et al., "Molecular Cloning of the Defense Factor in the Albumen Gland of the Sea Hare *Aplysia Kurodai*," *FEBS Letters* 377:373–376 (1995).

Yamazaki, "Antitumor and Antimicrobial Glycoproteins from Sea Hares," *Comp. Biochem. Physiol.* 105(C)(2): 141–146 (1993).

*Primary Examiner*—Karen Cochrane Carlson
(74) *Attorney, Agent, or Firm*—Albert P. Halluin; J. David Smith; Howrey Simon Arnold & White, LLP

(57) ABSTRACT

The present invention relates to a protein having an anti-tumoral effect, a DNA encoding such a protein, and a process for the preparation of such a protein as well as its use.

7 Claims, 1 Drawing Sheet

Fig. 1

SER GLU ALA SER GLY ASP TYR ILE LEU ILE ALA SER TYR ALA ASP

AGT CTC CGT AGT CCT CTA ATG TAT GAT TAT CGT AGA ATG CGT CTA
TCA GAG GCA TCA GGA GAT TAC ATA CTA ATA GCA TCT TAC GCA GAT

PROTEIN HAVING AN ANTI-TUMORAL EFFECT

FIELD OF THE INVENTION

This invention relates to a protein having anti-tumor activity, a DNA encoding the same, a process for the preparing the same and methods for treating malignancies such as cancers with the same.

BACKGROUND OF THE INVENTION

Chemotherapeutic agents are frequently used for treating malignancies including tumors. However, they do not have a selective effect, i.e. they not only attack the tumor to be treated, but they also attack healthy tissue which is in turn considerably damaged. Thus, it is desirable to provide anti-tumor agents for treating tumors selectively. It is an object of the present invention to provide such an agent.

SUMMARY OF THE INVENTION

The present invention relates to a protein having anti-tumor activity. The protein comprises the amino acid sequence of FIG. 1 or a biologically active analogue thereof having an amino acid sequence differing therefrom by one or several amino acids.

The present invention is based on the finding that a protein present in sea snails or hares, particularly in *Aplysia punctata*, kills tumor cells but not healthy cells. This protein comprises the amino acid sequence illustrated in FIG. 1 or a biologically active analogue thereof having an amino acid sequence differing therefrom by one or several amino acids.

BRIEF DESCRIPTION OF THE DRAWINGS

FIG. 1 shows the amino acid sequence comprised by a protein according to the invention and the base sequence derived therefrom.

DETAILED DESCRIPTION OF THE INVENTION

The present invention relates to a protein having anti-tumor activity. The protein comprises the amino acid sequence of FIG. 1 or a biologically active analogue thereof having an amino acid sequence differing therefrom by one or several amino acids.

The present invention is based on the finding that a protein present in sea snails or hares, particularly in *Aplysia punctata*, kills tumor cells but not healthy cells. This protein comprises the amino acid sequence illustrated in FIG. 1 or a biologically active analogue thereof having an amino acid sequence differing therefrom by one or several amino acids.

The expression "amino acid sequence differing therefrom by one or several amino acids" refers to the fact that the amino acid sequence of FIG. 1 may include additions, deletions, inversions and/or substitutions of one or several amino acids.

A protein according to the invention can be provided by common methods. It is preferable to slightly squeeze a sea snail *A. punctata* which then supplies a blue-dark violet secretion. This secretion is diluted with PBS and subjected to differential centrifugation. Thereafter, it is salted out in a fractional manner using ammonium sulfate and subjected to ion exchange chromatography on a DE-52 column as well as polyacrylamide gel electrophoresis. The separated proteins are partially transferred to a PVDF membrane and colored by means of sulforhodamine B. In accordance with the visible bands, the proteins are cut out of the gel and tested for their anti-tumor effect over tumor cells. A protein according to the invention, which has a selective effect against tumor cells, may then be identified.

The present invention also relates to a nucleic acid coding for a protein according to the present invention. The nucleic acid may be an RNA or a DNA. The latter may be, e.g. a genomic DNA or a cDNA. The following DNA is preferred:

(a) a DNA according to FIG. 1 or a DNA differing therefrom by one or several base pairs, (b) a DNA hybridizing with the DNA of (a), or (c) a DNA related to the DNA of (a) or (b) according to the degeneracy of the genetic code.

The expression "hybridizing DNA" refers to a first DNA which hybridizes with a second DNA under normal conditions, particularly at 20° C. below the melting point of the DNA.

For the preparation of a DNA according to the present invention, it is preferable to use a cDNA expression library as a basis which is prepared from the mRNA of a sea snail or hare, preferably *A. punctata*. Such a library can be screened with polyclonal antibodies and monoclonal antibodies, respectively, which are directed against a protein according to the invention. Such antibodies may be prepared by common methods. Positive clones may be identified by screening. They can be subcloned and sequenced so as to identify a DNA according to the invention.

A DNA according to the invention can be present in a vector and expression vector, respectively. A person skilled in the art is familiar with examples thereof. In the case of an expression vector for *E. coli* examples include $\lambda$gt11, pGEMEX, pUC derivatives, pGEX-2T, pET3b and pQE-8. For the expression in yeast, examples include pY100, Ycpad1, pKCR, pEFBOS, cDM8 and pCEV4. A baculovirus expression vector, pAcSGHisNT-A, is especially suitable for expression in insect cells.

Those of skill in the art are familiar with suitable cells to express a DNA according to the present invention which is present in an expression vector. Examples of such cells include the *E. coli* strains HB101, DH1, x1776, JM101, JM109, BL21 and SG13009, the yeast strain *Saccharomyces cerevisiae* and the animal cells L, 3T3, FM3A, CHO, COS, Vero and HeLa as well as the insect cells Sf9.

Those skilled in the art also know how to insert a DNA according to the present invention into an expression vector. This DNA may be inserted in combination with a DNA coding for another protein or peptide so that the DNA according to the invention can be expressed in the form of a fusion protein.

In addition, those skilled in the art also know conditions for cultivating transformed cells and transfected cells, respectively. Likewise, processes for isolating and purifying an expressed protein are known to skilled artisans. Thus, a recombinantly produced protein according to the present invention may be a fusion protein.

A further aspect of the present invention relates to an antibody directed against a protein or fusion protein of the present invention. Such an antibody can be prepared by methods known to those of skill in the art. It may be polyclonal or monoclonal. To prepare such antibodies, it is favorable to immunize animals particularly rabbits or chickens for a polyclonal antibody and mice for a monoclonal antibody with a fusion protein or fragments thereof. Further "boosters" can be effected with the same fusion protein or fragments thereof. A polyclonal antibody may then be obtained from serum or egg yolk of the animal. For preparing a monoclonal antibody, animal spleen cells are fused with myeloma cells according to techniques well known to skilled artisans.

Proteins according to the present invention are unique in their ability to kill tumors selectively. Healthy cells are not significantly affected by them. This makes the present invention extraordinarily significant for the treatment of tumors and malignancies. Furthermore, the proteins according to the present invention also demonstrate an antiviral effect. Thus, they are also useful for treating viral diseases. In addition, proteins according to the invention can be used for diagnostic purposes.

Moreover, antibodies according to the present invention may be used to investigate the mode of action of the above proteins. Thus, it is possible to even increase the selectivity and activity of these proteins.

The nucleic acids of the present invention can be used for therapeutic measures. For example, the nucleic acids can be inserted in common expression vectors, and the latter can be introduced into persons suffering from a tumor or malignancy. In this method of treatment, it is favorable to introduce the nucleic acids directly into a tumor. The proteins which kill the tumor selectively are expressed in the body and/or in the tumor by the expression of the nucleic acids.

The following examples further illustrate the present invention but are not to be construed as being limiting.

EXAMPLE 1

Isolating a Protein According to the Invention

The sea snail *Aplysia punctata* was slightly squeezed and, as a result, supplied a blue-dark violet secretion. This secretion was diluted with PBS at the rate of 1:10. The dilute secretion was subjected to differential centrifugation, fractional salting-out using ammonium sulfate in a common buffer, and ion exchange chromatography on a DE-52 column (eluent: buffer, pH 7.2, continuous NaCl gradient of 10 mM to 1 mM NaCl). Thereafter, polyacrylamide gel electrophoresis was carried out using a 10% polyacrylamide gel. The separated proteins were partially transferred to a PVDF membrane and colored using sulforhodamine B. In accordance with the visible bands, the individual proteins were cut out of the gel and tested for their anti-tumor effect. For this purpose, they were incubated with tumor cells, and tumor cell destruction, such as contraction of the cells, was awaited.

A protein according to the invention was identified. Sequencing showed that this protein comprises the amino acid sequence of FIG. 1.

EXAMPLE 2

The Effect of a Protein According to the Invention on Tumor Cells and Healthy Cells The protein described in Example 1 was incubated with the following cell lines:

T47 cells (human breast cancer)

HeLa cells (human uterine carcinoma)

A-204 cells (human rhabdomyosarcoma)

After 3 hours, these cell lines showed the first signs of destruction, i.e. contraction and loss of surface adhesion became identifiable. The cells were destroyed after 4 to 5 hours.

In contrast thereto, healthy cells were not significantly affected by a protein according to the present invention. For example, the motility and the fertilization potential of sperm cells as well as the fertilization potential of egg cells were not affected. In addition, no effects on previously inseminated egg cells, e.g. monocellular embryos, were observed when a protein according to the present invention was microinjected into them. Moreover, no disadvantageous effects were observed when a protein according to the present invention was directly injected into the following living organisms: sea anemone, starfish, turbot and mouse. Furthermore, no disadvantageous effects were observed when a protein according to the present invention was placed directly into open wounds of humans.

The above experiments demonstrate that a protein according to the present invention kills tumors selectively but does not significantly affect healthy tissue.

While this invention has been described with respect to some specific embodiments, it is understood that modifications thereto and equivalents and variations thereof will be apparent to one skilled in the art and are intended to be and are included within the scope of the claims appended hereto.

---

What is claimed is:

1. An isolated and purified protein having anti-tumor activity, wherein said protein comprises the peptide sequence described in SEQ ID NO:1.

2. An isolated and purified nucleic acid molecule, wherein said nucleic acid molecule encodes the protein of claim 1.

3. The nucleic acid molecule of claim 2, wherein said nucleic acid molecule comprises nucleotides 46 to 90 of SEQ ID NO:2.

4. An expression plasmid comprising the nucleic acid molecule of claim 2 or of claim 3.

5. A host cell transformed with the plasmid of claim 4.

6. A method for the production of the protein of claim 1, wherein said method comprises culturing the host cell of claim 5 under conditions that result in the expression of the said protein, and isolating the protein from the host cell.

7. A method of treating cancer, wherein said method comprises administering to a subject the protein of claim 1.

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Aplysia punctata

<400> SEQUENCE: 1

Ser Glu Ala Ser Gly Asp Tyr Ile Leu Ile Ala Ser Tyr Ala Asp
1               5                   10                  15

<210> SEQ ID NO 2
<211> LENGTH: 90
<212> TYPE: DNA
<213> ORGANISM: Aplysia punctata

<400> SEQUENCE: 2
agtctccgta gtcctctaat gtatgattat cgtagaatgc gtctatcaga ggcatcagga      60
gattacatac taatagcatc ttacgcagat                                      90
```